United States Patent [19]

Kulin et al.

[11] 4,295,619
[45] Oct. 20, 1981

[54] SOLUTION CONTAINER HANGER

[75] Inventors: Ralph Kulin, Marengo; Ronald C. Stauber, Hawthorn Woods, both of Ill.

[73] Assignee: Baxter Travenol Laboratories, Inc., Deerfield, Ill.

[21] Appl. No.: 93,356

[22] Filed: Nov. 13, 1979

[51] Int. Cl.³ .................................................. B65B 67/12
[52] U.S. Cl. ...................................... 248/95; 248/311.3; 248/318
[58] Field of Search ................... 248/95, 97, 100, 126, 248/150, 214, 311.3, 318

[56] References Cited

U.S. PATENT DOCUMENTS

| | | | |
|---|---|---|---|
| 973,414 | 10/1910 | Eastham | 248/100 |
| 1,414,234 | 5/1922 | Duke | 248/163 A X |
| 1,714,308 | 5/1929 | Gunderson | 248/95 X |
| 2,235,182 | 3/1941 | Weston | 248/100 |
| 2,959,386 | 11/1960 | Garth | 248/95 |
| 3,529,598 | 9/1970 | Waldman | 248/95 X |
| 3,638,888 | 2/1972 | Ross | 248/97 |
| 4,027,842 | 6/1977 | Mittleman | 248/95 X |

FOREIGN PATENT DOCUMENTS 317395   1/1957   Switzerland ...................... 248/150

*Primary Examiner*—William H. Schultz
*Attorney, Agent, or Firm*—Paul C. Flattery; George H. Gerstman

[57] ABSTRACT

A solution container hanger for use in infusion or drain of a solution from a patient, foldable for storage or transportation. The hanger comprises two basic parts: a first member and a second member rotationally affixed to the first member to enable the hanger to be placed in an infusion, drain, or storage position. Hanger means are attached to the second member to enable the solution container hanger to be hung from a door or other elevated structure for infusion of a solution. Support means are attached to the first and second members from which a solution container is hung for infusion or drain. The first and second members are positioned substantially perpendicular in a drain position and substantially parallel in an infusion or storage position.

6 Claims, 6 Drawing Figures

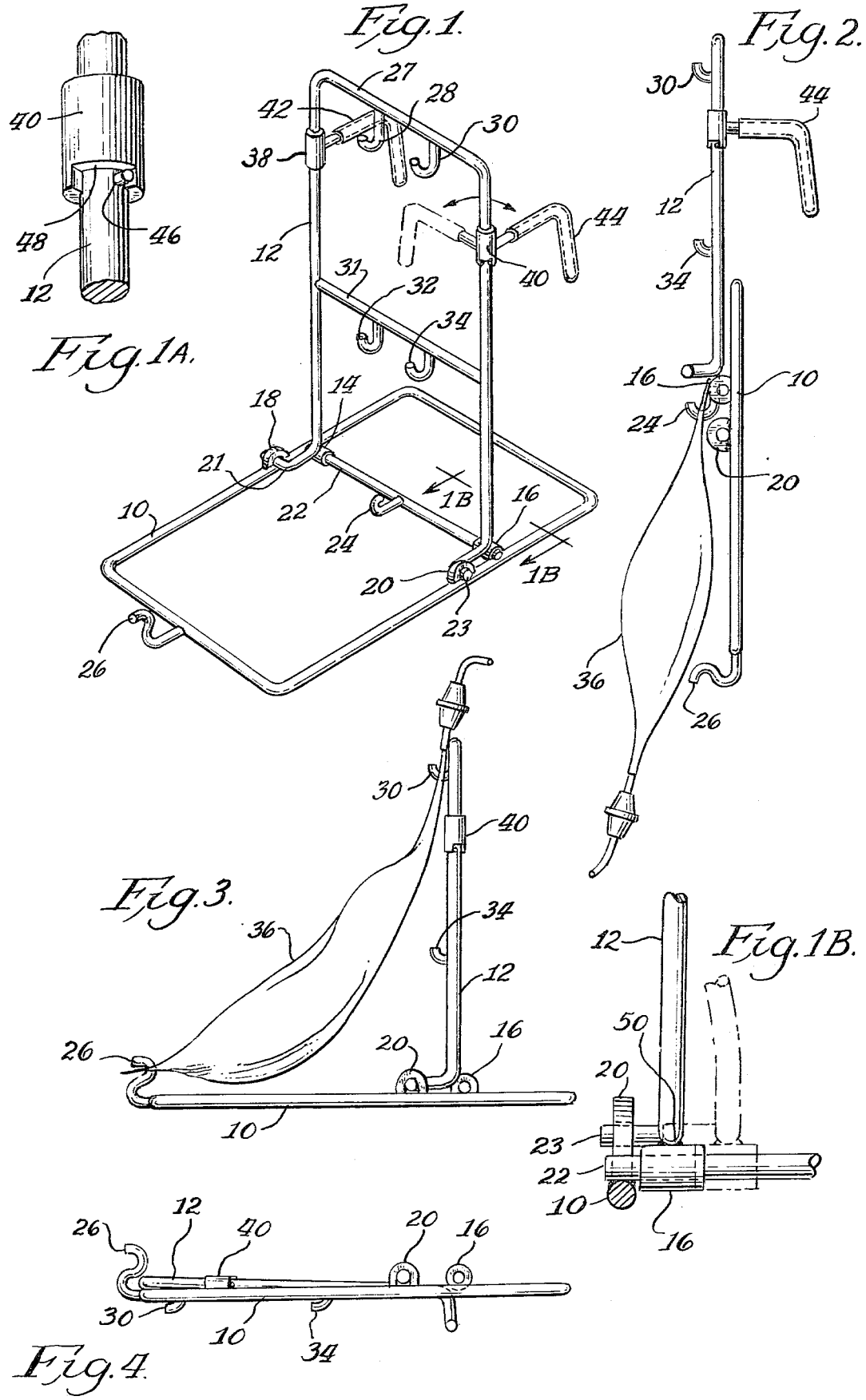

SOLUTION CONTAINER HANGER

BACKGROUND OF THE INVENTION

This invention relates to a solution container hanger, principally for use in conjunction with a peritoneal dialysis solution container.

Currently, the most widely used method of kidney dialysis for treatment of End Stage Renal Disease (ESRD) is "hemodialysis". Here, the patient's blood is cleansed by passing it through an artificial kidney in an artificial kidney dialysis machine. By the process of diffusion across a semipermeable membrane is the artificial kidney, impurities and toxins are removed from the patient's blood to thereby perform a natural function of the patient's kidneys. Hemodialysis is generally required three times a week, each dialysis requiring 4-5 hours in a dialysis center or at home. During dialysis, the patient is "tied" to the machine by venous and arterial blood lines which convey his blood to and from the artificial kidney.

Although used less frequently than hemodialysis, a procedure known as "intermittent peritoneal dialysis" is an accepted method for treating ESRD. In this procedure, a dialysis solution is infused into the patient's peritoneal cavity by means of tubing and a catheter. The peritoneum, which defines the peritoneal cavity, contains many small blood vessels and capillary beds which act as a natural semipermeable membrane. This natural membrane may be contrasted with the artificial membrane used in hemodialysis. In both cases, however, impurities and toxins in the blood are removed by diffusion across a membrane—a cellulose membrane of an artificial kidney or a peritoneal membrane of a peritoneal cavity.

In intermittent peritoneal dialysis, dialysis solution remains in the patient's peritoneal cavity for a time sufficient for blood impurities to be removed by diffusion across the peritoneal membrane and into the dialysis solution. The impurity containing dialysis solution then is drained from the peritoneal cavity by means of a catheter and tubing, and a fresh supply of dialysis solution is infused. Intermittent peritoneal dialysis utilizes pumps or other auxillary equipment to which the patient is "tied" during dialysis; here also the patient must remain sedentary.

"Continuous ambulatory peritoneal dialysis" is another type of peritoneal dialysis which uses the peritoneum as a semipermeable membrane. The continuous procedure has the important advantage, however, of enabling the patient to be ambulatory and conduct a normal routine during dialysis. The patient is not "tied" to a machine and he must be sedentary only for the time period required to drain and infuse dialysis solution from and into the peritoneal cavity. This infusion and draining is handled by tubing and a surgically implanted, indwelling catheter in the patient's abdominal wall and in communication with his peritoneal cavity.

The continuous ambulatory peritoneal dialysis procedure is intended to be a patient self-care technique once the catheter is surgically implanted. Thus, it is important that the apparatus involved, e.g., tubing and solution container and ancillary equipment such as the present invention, be simple and easy to use. The present invention is intended to simplify the procedure for infusing and draining dialysis solution, the invention being useful in the home or other location as well as in a medical facility. The invention concerns a novel solution container hanger which is portable and may be hung from a door or other elevated structure for infusion of the dialysis solution and moved to a low position, for example, the floor, to permit drain. The invention is also easily folded for carrying or storage.

A support for surgical bags and drain tubes for attachment to the sides of hospital beds is disclosed in Garth U.S. Pat. No. 2,959,386. Here a support fabricated from wire is attached to the side of a hospital bed for hanging a urinary drain bag or other medical drain bag to receive body effluent. Unlike the hanger disclosed in Garth, the present invention is suitable for other than a hospital environment and can be placed into three positions: (1) infusion; (2) drain; and (3) storage or carrying.

A foldable leaf bag holder is shown in Ross U.S. Pat. No. 3,638,888 which supports a plastic bag in a vertical or horizontal position. The device in Ross is always utilized on the ground unlike the present invention which is intended to be hung from a door or other elevated structure for infusion of solution. A butchering stand is disclosed in Duke U.S. Pat. No. 1,417,234, which is foldable for storage, but does not permit meat to be butchered in more than one position. The butchering stand is cumbersome and its and Ross' design would not be adaptable, as the present invention is, for support of a solution container in infusion and drain.

None of the prior art hangers satisfy the following criteria for a solution container hanger adaptable for use in continuous ambulatory peritoneal dialysis: (1) able to be easily folded for storage and transportation in a small size; (2) able to be suspended from a height necessary for infusion of dialysis solution; and (3) able to be placed at a position low enough for drainage of the dialysis solution. Thus, there is a need to provide a solution container hanger which is portable and can be positioned in either an infusion or drain position. A solution container hanger which is simple in design is also desirable for ease of manufacture.

With the advent of dialysis solutions contained in plastic bags, and the development of continuous ambulatory peritoneal dialysis, a simple solution container hanger for use by patients in and outside of a hospital environment is desired. A simple, effective, inexpensive solution container hanger is important, particularly from a patient self-care standpoint, when practicing continuous ambulatory peritoneal dialysis. It is therefore, an object of this invention to provide a solution container hanger which is simple, effective, inexpensive, easily portable, and can be placed in a drain, infusion, or storage position.

As will be fully explained below, the present invention is easy to operate. Ease of operation is important for the practice of continuous ambulatory peritoneal dialysis because of the large number of patients with limited physical capacity because of poor eyesight, weakness, arthritis and the like. This invention also is particularly advantageous for use by children and geriatric patients for these same reasons.

SUMMARY OF THE INVENTION

The solution container hanger of the present invention comprises two basic parts, preferably fabricated of a rigid steel or aluminum wire: a first member and a second member rotationally affixed to the first member to enable the solution container hanger to be placed in an infusion, drain, or storage position. The second member has attached to it a hanger means to enable the solution container hanger to be suspended from a door or other elevated structure for infusion. Support means are attached to the first member to suport a solution container in an infusion position, and support means are attached to the second member to support a solution container in a drain or infusion position. Since the second member is rotationally affixed to the first member, the entire solution container hanger can be folded for storage or transportation. Also, the hanger means which is attached to the second member is preferably rotatable about the second member so that the hanger means can be folded for efficient storage and transportation. When the hanger is in a drain position, the first and second members are substantially perpendicular; when in an infusion or storage position, the members are substantially parallel.

BRIEF DESCRIPTION OF THE DRAWINGS

Other objects, features and advantages of the present invention will become more fully apparent from the following detailed description of the preferred embodiment, the appended claims and the accompanying drawings in which:

FIG. 1 is a perspective view of the solution container hanger of the present invention in a drain position;

FIG. 1A is an enlarged perspective view of the rotation means of the preferred embodiment of the present invention which attaches the hanger means to the second member of the present invention;

FIG. 1B is an enlarged end view of an element of the second member of the present invention shown in a locked position for drainage of solution and the second member shown in phantom in a position for moving the solution container hanger to an infusion or storage position;

FIG. 2 is a side view of the solution container hanger of the present invention shown in the infusion position;

FIG. 3 is a side view of the solution container hanger of the present invention shown in the drain position; and FIG. 4 is a side view of the solution container hanger of the present invention shown in a storage or transportation position.

DETAILED DESCRIPTION OF THE PREFERRED EMBODIMENT

The preferred embodiment of the hanger of this invention is illustrated by way of example in FIGS. 1-4.

Referring to FIG. 1, the solution container hanger of the present invention is shown in perspective with a generally rectangular first member 10 and a generally rectangular second member 12 rotationally affixed to first member 10 at collars 14 and 16 which rotate around first member 10 at support strut 22. Second member 12 is slidably engaged by means of prongs 21 and 23 in member 10 at washer connections 18 and 20. First member 10 has a cross support strut 22 upon which collars 14 and 16 rotate and slide when pressure is applied inwardly to second member 12 below strut 31 to disengage member 12 from washer connections 18 and 20 for moving the solution container hanger to an infusion position as shown in FIG. 2 or a folded position as shown in FIG. 4. The configuration shown in FIGS. 1 and 3 is the solution container hanger of the present invention in the drain position. The rotation of second member 12 around first member 10 places the members in a substantially perpendicular position for drain and a substantially parallel position for infusion and storage.

First member 10 has a hook 24 suspended from support strut 22 for hanging a solution container preferably in the infusion position as shown in FIG. 2. First member 10 also has a S-shaped hook 26 suspended from first member 10's bottom for support of the solution container off of the floor in the drain position as shown in FIG. 3.

Second member 12 has suspended from support struts 27 and 31 a plurality of hooks 28, 30, 32, and 34 for support of a solution container in the drain position as shown in FIG.3. Hooks 28, 30, 32, and 34 can also be used for support of a solution container in the infusion position of FIG. 2. Typically, in the drain position, the solution container will be suspended from either hooks 32 and 34 or hooks 28 and 30, but it can be readily seen that it is possible to suspend the solution container from one of the hooks. A solution container which would use this invention is shown as 36 in FIGS. 2 and 3. Such a container for use in continuous ambulatory peritoneal dialysis is marketed by Baxter Travenol Laboratories, Inc., of Deerfield, Ill. as an AMBU-FLEX TM container. The AMBU-FLEX TM container has two holes for use in the drain position, and therefore, it is preferable when the AMBU-FLEX TM container is used in conjunction with the present invention that two hooks be used in the drain position to correspond with the two holes in the container. Second member 12 has affixed to it at collars 38 and 40 hangers 42 and 44 preferably rotationally attached to second member 12 so that hangers 42 and 44 may be rotated inwardly when not in use. The hangers 42 and 44 are used in the infusion position to hang from a door or other elevated structure and preferably are covered with a plastic or other smooth coating to prevent scratching of a door or other fixture.

Referring to FIG. 1A, second member 12 is shown with rotationally affixed collar 40 which rotates around second member 12 and has attached hanger 44 as shown in FIG. 1. Second member 12 has a projection 46 that enables collar 38 to rotate a maximum of 90° inwardly for storage of the solution container hanger. Collar 40 has a cutaway portion 48 which permits and confines rotation to 90° around second member 12. Collar 38 is the same configuration as collar 40.

Referring to FIG. 1B, a partial cross sectional end view of second member 12 is shown engaged in washer connection 20 and preferably spot welded to collar 16 at point 50. When second member 12 is squeezed inwardly, preferably by manual pressure, below strut 31, prong 23 slides out of engagement with washer connection 20 into the position shown in phantom in FIG. 1B so that the solution container hanger may be moved into the infusion position of FIG. 2 or the storage position of FIG. 4. Collar 14, washer connection 18 and prong 21 are of the same configuration.

While the present invention has been disclosed in connection with the preferred embodiment thereof, it should be understood that there may be other embodiments, which fall within the sphere and scope of this invention as defined by the following claims.

What is claimed is:

1. A solution container hanger comprising:
   (a) a first member;
   (b) a second member rotationally affixed to the first member to enable the solution container hanger to be placed in an infusion, drain, or storage position;
   (c) support means attached to the first member to suspend and support a solution container in an infusion position in which the first and second members are substantially parallel;

(d) support means attached to the second member to suspend and support a solution container in a drain or infusion position in which the first and second members are substantially perpendicular in a drain position and substantially parallel in an infusion position; and (e) hanger means attached to the second member to enable the solution container hanger to be hung in an infusion position from a door or other elevated structure.

2. The solution container hanger of claim 1 wherein the first member is rectangular in shape with a support strut with an attached hook for support of a solution container in an infusion position.

3. The solution container hanger of claim 1 wherein the second member is rectangular in shape with support struts with an attached plurality of hooks for support of a solution container in a drain or infusion position.

4. The solution container hanger of claim 1 wherein the second member is attached to two collars which rotate around the support strut of the first member after prongs on the second member are slidably removed from washer connections on the first member to enable the solution container hanger to be moved to an infusion or storage position, the first and second members being substantially parallel in an infusion or storage position.

5. The solution container hanger of claim 1 wherein the hanger means are attached to two collars which rotate 90° around the second member to permit positioning of the hanger means in a position for infusion or storage.

6. The solution container hanger of claim 1 wherein the first member has attached thereto an S-shaped hook for support of the bottom of the solution container off the floor or other low position during drain.

* * * * *